United States Patent [19]

Liang et al.

[11] Patent Number: 5,777,179
[45] Date of Patent: Jul. 7, 1998

[54] CO-PRODUCTION OF PERFLUOROMETHYL PERFLUOROVINYL ETHER AND PERFLUOROETHYL PERFLUOROVINYL ETHER

[75] Inventors: Baishen Liang, Newark; Ming-Hong Hung, Wilmington, both of Del.; Paul Raphael Resnick, Cary, N.C.

[73] Assignee: E. I. du Pont de Nemours and Company, Wilmington, Del.

[21] Appl. No.: 655,347

[22] Filed: May 24, 1996

[51] Int. Cl.$^6$ .................................. C07C 41/02
[52] U.S. Cl. .................................. 568/685
[58] Field of Search .................................. 568/685

[56] References Cited

U.S. PATENT DOCUMENTS

| | | | |
|---|---|---|---|
| 3,114,778 | 12/1963 | Gerhard et al. | 260/614 |
| 3,180,895 | 4/1965 | Harris, Jr. | 260/614 |
| 3,250,808 | 5/1966 | Moore, Jr. et al. | 260/535 |
| 3,291,843 | 12/1966 | Fritz | 260/614 |
| 3,321,532 | 5/1967 | Lorenz | 260/614 |
| 4,035,388 | 7/1977 | Martini | 260/340.6 |
| 4,081,466 | 3/1978 | Resnick | 260/544 |
| 4,118,421 | 10/1978 | Martini | 260/543 |
| 4,554,112 | 11/1985 | Ezzell et al. | 260/543 |
| 4,749,526 | 6/1988 | Flynn | 260/544 |
| 4,772,756 | 9/1988 | Bornengo et al. | 568/684 |

FOREIGN PATENT DOCUMENTS

| | | |
|---|---|---|
| 0 647 609 A1 | 5/1993 | European Pat. Off. |
| 2-4733 | 1/1990 | Japan . |
| HEI 4-139145 | 5/1992 | Japan . |
| 61140539 | 9/1993 | Japan . |
| 04159246 | 10/1993 | Japan . |
| 0514-7492 | 7/1980 | U.S.S.R. . |

*Primary Examiner*—Marianne M. Cintins
*Assistant Examiner*—Dwayne C. Jones

[57] ABSTRACT

A process for the production of perfluoromethyl perfluorovinyl ether (PMVE) and perfluoroethyl perfluorovinyl ether (PEVE) from hexafluoropropylene epoxide (HFPO) and a mixture comprising carbonyl fluoride (CF) and perfluoroacetyl fluoride (PAF) is disclosed. The process includes a step (a) involving the reaction of hexafluoropropylene epoxide (HFPO) with a mixture of carbonyl fluoride (CF) and perfluoroacetyl fluoride (PAF) to produce a mixture of 2,3,3,3-tetrafluoro-2-(trifluoromethoxy)propionic acid fluoride (PMPF) and 2,3,3,3-tetrafluoro-2-(pentafluoroethoxy)propionic acid fluoride (PEPF). In a second step, a mixture of PMPF and PEPF made in the step (a) is dehalocarbonylated to produce a mixture of PMVE and PEVE.

18 Claims, 1 Drawing Sheet

CO-PRODUCTION OF PERFLUOROMETHYL PERFLUOROVINYL ETHER AND PERFLUOROETHYL PERFLUOROVINYL ETHER

FIELD OF THE INVENTION

The present invention relates to a process for the co-production of perfluoromethyl perfluorovinyl ether (PMVE) and perfluoroethyl perfluorovinyl ether (PEVE) by reaction of hexafluoropropylene epoxide (HFPO) with a mixture of carbonyl fluoride (CF) and perfluoroacetyl fluoride (PAF), especially a mixture of CF and PAF which is a by-product of the manufacture of a perfluorinated epoxide such as HFPO.

BACKGROUND OF THE INVENTION

Fluoroalkyl perfluorovinyl ethers of the formula $R_fOCF=CF_2$, wherein RF is a fluorine-containing organic radical, have found extensive use as comonomers for preparation of fluoroplastics and fluoroelastomers. Fluoroalkyl perfluorovinyl ethers are known to copolymerize with alkenes such as ethylene, tetrafluoroethylene (TFE), chlorotrifluoroethylene, vinylidene fluoride, vinyl fluoride, propene and hexafluoropropene (HFP). Of particular interest and significant application are copolymers formed by copolymerization of TFE with perfluoroalkyl perfluorovinyl ethers. These copolymers are commonly referred to as PFA (perfluoroalkoxy) copolymers and are useful for producing high-quality electrical insulation and molded components.

One of the widely-used fluoroalkyl perfluorovinyl ethers is perfluoropropyl perfluorovinyl ether (PPVE). PPVE is typically manufactured commercially by the dimerization of hexafluoropropylene epoxide (HFPO) followed by a dehalocarbonylation reaction. HFPO for PPVE manufacture and other uses is sometimes produced commercially by the reaction of hexafluoropropylene (HFP) with oxygen. However, this HFPO production process is not without shortcomings since, regardless of the conditions employed, molar yields of HFPO are typically not greater than 50–60% due to the formation of by-products including CF, PAF and perfluorooxyalkylene carboxylic acid fluorides. These by-products including the CF and PAF have, in most instances, been considered waste and were disposed of as such. Accordingly, the HFP is not efficiently utilized in this process and the generation of significant quantities of waste is not desirable due to the cost of a safe and environmentally acceptable disposal.

SUMMARY OF THE INVENTION

This invention provides a process for producing the perfluoroalkyl perfluorovinyl ethers perfluoromethyl perfluorovinyl ether (PMVE) and perfluoroethyl perfluorovinyl ether (PEVE) from a mixture of carbonyl fluoride (CF) and perfluoroacetyl fluoride (PAF). The process includes the steps of:

(a) contacting an initial mixture comprising carbonyl fluoride (CF) and perfluoroacetyl fluoride (PAF) with hexafluoropropylene epoxide (HFPO) under conditions which form a mixture comprising 2,3,3,3-tetrafluoro-2-(trifluoromethoxy)propionic acid fluoride (PMPF) and 2,3,3,3-tetrafluoro-2-(pentafluoroethoxy)propionic acid fluoride (PEPF); and (b) dehalocarbonylating an intermediate mixture comprising 2,3,3,3-tetrafluoro-2-(trifluoromethoxy)propionic acid fluoride (PMPF) and 2,3,3,3-tetrafluoro-2-(pentafluoroethoxy)propionic acid fluoride (PEPF) formed in step (a) to form a product mixture comprising perfluoromethyl perfluorovinyl ether (PMVE) and perfluoroethyl perfluorovinyl ether (PEVE).

In a preferred form of the invention, the initial mixture is formed from the reaction of a perfluorinated alkene with oxygen, most preferably in which the CF and PAF is a by-product of the manufacture of a perfluorinated epoxide such as HFPO.

DETAILED DESCRIPTION

Figure 1:
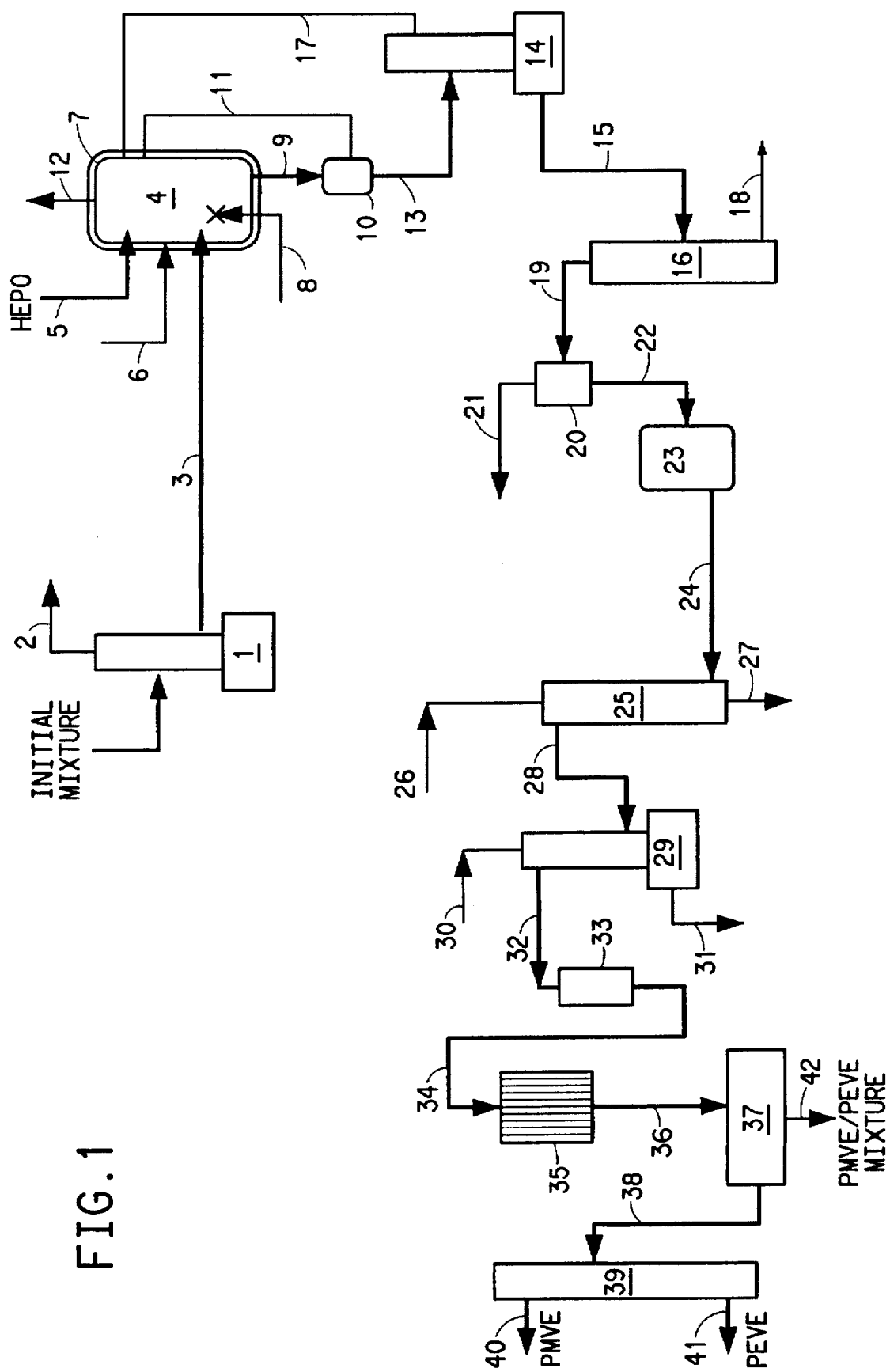
FIG. 1 is a schematic view of one preferred configuration of apparatus which may be employed to practice the present invention.

In the initial mixture for use in the present invention, the percentages of CF and PAF and their relative proportions can vary widely depending on available feedstocks and/or the desired PMVE/PEVE product mix. Surprisingly, invention provides a highly productive process in which PMVE and PEVE are concurrently formed in high yield from initial mixtures in which CF/PAF mole ratios range from 0.01 to 100. Preferably, the CF/PAF mole ratio in the initial mixture is about 0.1 to about 10. Most preferably, the mole ratio is about 0.3 to about 3.

The initial mixture comprising CF and PAF of step (a) of a process in accordance with the invention is preferably formed by liquid or gas phase oxidation of a perfluorinated alkene. Preferred perfluorinated alkenes have the formula $R^1R^2C=CR^3R^4$, wherein $R^1$, $R^2$, $R^3$, and $R^4$ are the same or different and are selected from the groups F and perfluoroalkyl radicals of formula $C_xF_{2x+1}$ wherein x is 1 to 6. The process is advantageously employed with an initial mixture obtained from the liquid or gas phase reaction of HFP and/or TFE with $O_2$.

In one preferred form of the present invention, the initial mixture is obtained as a by-product of the liquid phase reaction of perfluorinated alkenes with $O_2$ to make epoxides, most preferably HFP with $O_2$ to make HFPO. In addition to forming HFPO, the liquid phase reaction of HFP with $O_2$ yields significant quantities of CF and PAF and also somewhat lower percentages of perfluorooxyalkylene carboxylic acid fluoride compounds of formulas $CF_3O(CF_2O)_mCOF$ and $CF_3O(CF_2O)_mCF_2COF$, wherein m =0 through 100. A mixture of CF, PAF, and perfluorooxyalkylene carboxylic acid fluoride compounds (also containing small quantities of HFPO and unreacted HFP and $O_2$) is easily separated as a low boiling fraction from the process stream containing the HFPO. It has been discovered that this low boiling fraction containing CF and PAF, which has generally been considered as waste, is advantageously used directly as the initial mixture for a process of the invention. Preferably, excess oxygen is removed from the initial mixture when formed from this by-product stream. For example, when used as the initial mixture, good results can be obtained by the present process when the following quantities are present: CF—5 to 95 mole %; PAF—5 to 95 mole %; perfluorooxyalkylene carboxylic acid fluorides with m=0 or 1 up to 10 mole %; $O_2$ up to 5 mole %. In addition, HFP may be present in the initial mixture and has minimal impact on the process of step (a) as it is unreactive under step (a) conditions. However, it is preferred that the initial mixture contain less than about 5 mol % HFP due to the fact that HFP is more difficult to separate from intermediate mixture and product mixture streams than from the initial mixture, and HFP can lead to fouling of the process of step (b). HFPO may be present in the initial mixture but typically comprises less than about 5 mol % of the initial mixture due to the fact that HFPO is removed under conditions which are used to remove HFP. If desired, some or all of the other compounds may be separated from the CF and PAF mixture by standard separation techniques to provide an initial mixture containing higher percentages of CF and PAF.

In another preferred form of the invention, the initial mixture is made by the gas phase oxidation of HFP with $O_2$. While a number of products are usually produced in this process including HFPO and the same carboxylic acid fluoride compounds which are produced in the liquid phase oxidation of HFP discussed above, PAF is the main product together with high quantities of CF. The product stream of this reaction containing CF and PAF can be used directly as the initial mixture. Preferably, this mixture is stripped of excess oxygen. For example, good results can be obtained when this product stream contains: CF—5 to 95 mole %; PAF—5 to 95 mole %; perfluorooxyalkylene carboxylic acid fluorides with m=0 or 1 up to 10 mole %; $O_2$ up to 5 mole %. In addition, HFP and HFPO may be present as previously discussed for the instance where the initial mixture is produced by oxidation of HFP in the liquid phase. If desired, some or all of the other compounds may be separated from the CF and PAF mixture by standard separation techniques to provide an initial mixture containing higher percentages of CF and PAF.

Contacting of the initial mixture of step (a) with HFPO to form an intermediate mixture comprising PMPF and PEPF can be carried out under a variety of conditions. This reaction for a preferred process in accordance with the invention may be represented generally by the following:

employing a |CF+PAF|/HFPO ratio of 0.5 results in an intermediate mixture primarily comprising PMPF/HFPO and PEPF/HFPO adducts and containing HFPO oligomers (mainly q=0–3). While the upper range of the |CF+PAF|/HFPO mole ratio may be greater than 10, no special benefit is obtained. It is most preferred for the |CF+PAF|/HFPO mole ratio of the present invention to be about 2 to about 10.

In a preferred form of the invention, a polar aprotic solvent is present when the initial mixture is contacted with HFPO in step (a) of the process. In addition to being polar and aprotic, the solvent should be non-reactive (i.e., not contain hydroxyl groups) and preferably solublize only the reactants, i.e., CF and PAF in the initial mixture, HFPO and catalysts (used in the preferred process). It is also preferred to use a solvent in which the PMPF and PEPF of the intermediate mixture are preferably insoluble or are minimally soluble which serves to minimize further reaction of the PMPF and PEPF with HFPO and therefore avoids formation of PMPF/HFPO and PEPF/HFPO adducts. In addition, the amount of solvent can be adjusted to promote the formation of PMPF and PEPF.

Preferred solvents are selected from the group comprising hydrocarbon nitriles such as acetonitrile, propionitrile and benzonitrile, ethylene glycol dialkyl ethers of formula $C_rH_{2r+1}(OCH_2CH_2)_sOC_rH_{2r+1}$ wherein r=1–3 and s=1–6 such as glyme, diglyme, triglyme, tetraglyme and tetraethylene glycol dimethyl ether, and nitro substituent-containing solvents such as nitromethane and nitrobenzene. Especially preferred solvents in the process of step (a) are the nitriles such as acetonitrile and benzonitrile and mixtures thereof. The amount of solvent employed in the contacting of the initial mixture with HFPO in step (a) of the present invention is preferably between 100:1 and 1:100 weight ratio of solvent to combined weight of CF+PAF+HFPO. In a pre-

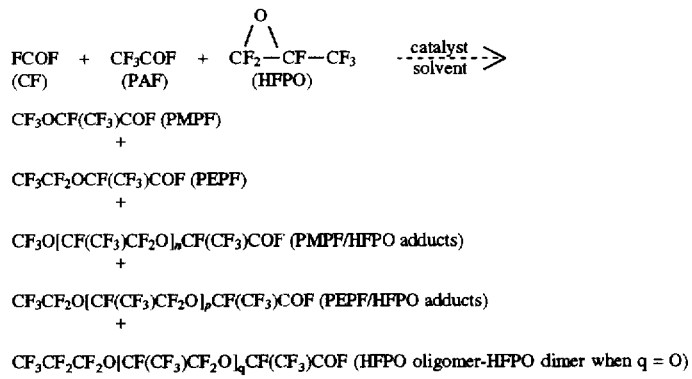

Preferably, conditions are employed which provide higher yields of PMPF and PEPF and lesser quanties of the PMPF/HFPO and PEPF/HFPO adducts. The mole ratio of |CF+PAF|/HFPO, the temperature of the reaction and, in a preferred process, the amount of catalyst as well as the amount and kind of solvent, influence the course, speed and direction of the reaction of the initial mixture with HFPO to produce the intermediate mixture. Generally, mole ratio of |CF+PAF|/HFPO bears more directly on the product mix than other factors. Preferably, this ratio is at least about 1, most preferably at least about 1.5. For example, holding other factors at preferred values, employing a |CF+PAF|/HFPO mole ratio of 1 or more results in an intermediate mixture rich in PMPF and PEPF, i.e., mole ratio in the intermediate mixture of PMPF and PEPF to PMPF/HFPO and PEPF/HFPO adducts being greater than 1.5, with minimal formation of HFPO oligomers. On the other hand, ferred embodiment, the solvent is acetonitrile and the weight ratio of acetonitrile to the combined weight of CF+PAF+HFPO is 3:7.

In a preferred process in accordance with the invention, a catalyst is used in step (a) of the process. Substantially any fluoride soluble in the solvent to the extent of at least 0.001 wt % at 20° C. and ionizable at the reaction temperatures may be used as a catalyst in step (a) of the present invention. Fluorides of the alkali, alkaline earth and transition metals from the set selected from groups IA (for example, LiF, NaF, KF, RbF, CsF), IIA (for example, BeF$_2$, MgF$_2$, CaF$_2$), IVA (for example, SnF$_2$), IB (for example, CuF$_2$, AgF) and IIB (for example, HgF$_2$) elements of a Standard Periodic Table of the Elements, such as that represented upon the inner front cover of Lang's Handbook of Chemistry, Fourteenth Edition, John A. Dean editor, McGraw Hill, Inc., 1992, are acceptable as catalysts. Especially suitable from this set are KF and CsF. A class of preferred catalysts are the tetraalkyl ammonium halides selected from the group represented by the formula $N(R^5R^6R^7R^8)X$, wherein $R^5$, $R^6$, $R^7$ and $R^8$ are the same or different and are linear or branched $C_1$ through $C_4$ alkyl radicals, and X is a halide such as fluoride, chloride, bromide or iodide. Preferred of the tetraalkyl ammonium halide catalysts is $N(CH_2CH_3)_4X$, wherein X is fluoride, chloride, bromide or iodide. The amount of tetraalkyl ammonium halide catalyst employed in step (a) of the present process is generally between 0.0001 and 0.01 mole per mole of HFPO and preferably between from 0.0005 to 0.005 mole per mole HFPO. In a preferred embodiment, the catalyst is $N(CH_3CH_2)_4Br$ and the amount employed is between 0.005 and 0.002 mole per mole of HFPO. Other catalysts of utility in step (a) of the present invention are described by Martini in U.S. Pat. No. 4,118,421 and U.S. Pat. No. 4,035,388, Resnick in U.S. Pat. No. 4,081,466, Flynn in U.S. Pat. No. 4,749,526, Okabe et al. in Japan kokai application 90-4,733, Fukasawa in Japan kokai applications 92-139,145 and 92159,246, and Takeo et al. in Japan kokai application 84-261,774.

The temperature at which the initial mixture is contacted with HFPO in step (a) has a controlling effect on the product mixture obtained. For example, low temperatures –20° C. to 30° C. favor the formation of PMPF and PEPF instead of the formation of PMPF/HFPO and PEPF/HFPO adducts and HFPO oligomer which are favored by higher temperatures, 50° C. and above. Reaction temperatures can range from –20° C. to 80° C., but reaction temperatures between 20° C. and 40° C. are preferred.

Generally, a variety of reaction pressures can be used in step (a) of the process ranging from subatmospheric through superatmospheric. Autogenous pressures can be used and such pressures typically range between from about 70 kPa to about 2400 kPa over the preferred temperature range. Higher pressures are preferred as the amount of gaseous reactants dissolved in the liquid solvent phase increases leading to an increased rate of production of the intermediate mixture. The reaction pressure can be controlled by regulating the rate of supply of gaseous reagents or venting of the reactor headspace.

In step (b) of the process in accordance with the present invention, the intermediate mixture of PMPF and PEPF is dehalocarbonylated to produce a product mixture comprising PMPE and PEVE. The reaction is represented generally by the following:

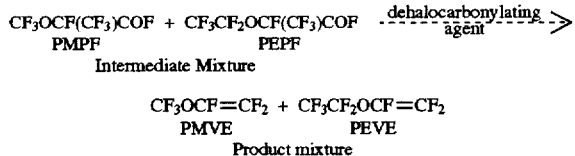

In a preferred process in accordance with the invention, the intermediate mixture is separated from other components of the mixture containing PMPF and PEPF formed in step (a) prior to said dehalocarbonylation in step (b). As has been discussed previously, step (a) of the process typically produces HFPO oligomers and PMPF/HFPO and PEPF/HFPO adducts in addition to PMPF and PEPF. In addition, solvents and/or catalysts are preferably used. Unreacted CF, PAF and HFPO may also be present. Standard separation techniques can be advantageously used to remove solvents, catalysts, and/or unreacted starting materials and recycle them for use in step (a). HFPO oligomers and PMPF/HFPO and PEPF/HFPO adducts, if present in significant quantity, should also be removed and typically are treated as waste.

In a preferred embodiment of step (b) of the present invention, dehalocarbonylation of the intermediate mixture is carried out by contacting the intermediate mixture with a dehalocarbonylating agent, preferably a solid oxygen-containing salt of an alkali or alkaline earth metal which is thermally stable at reaction conditions. Alkali or alkaline earth metals consist of the group IA and IIA elements of the Standard Periodic Table of the Elements. The oxygen-containing salts of the alkali metals lithium, sodium, potassium, rubidium and cesium are especially useful such as alkali metal carbonates, sulfates, sulfites, phosphates, phosphites, nitrates, nitrites, silicates and mixtures thereof. The most preferred dehalocarbonylating agents are the alkali metal carbonates and phosphates, with sodium carbonate ($Na_2CO_3$) being a particularity preferred carbonate and trisodium phosphate ($Na_3PO_4$) being a particularity preferred phosphate. Mixtures of these preferred agents are also useful in dehalocarbonylation of the intermediate mixture.

The oxygen-containing alkali metal salts employed as dehalocarbonylating agents in step (b) of the present invention are preferred to be thoroughly dried before use inasmuch as moisture promotes competing side reactions which yield products such as hydrofluoroalkyl ethers. The dehalocarbonylating agents are also preferably free of acidic hydrogen-containing species such as bicarbonate ($HCO_3^-$), dibasic phosphate ($HPO_4^{2-}$) and monobasic phosphate ($H_2PO_4^{1-}$).

While any convenient technique may be utilized to effect contacting of dehalocarbonylating agent with the intermediate mixture, a preferred embodiment of step (b) is to use a gaseous intermediate mixture which is passed through a bed of solid dehalocarbonylating agent heated to a temperature of from 75° C. to 400° C. Preferably, said temperature range is from about 150° C. to about 350° C. which achieves high yields of PMVE and PEVE in the product mixture while producing smaller quantities of undesirable by-products. When alkali metal carbonate and/or phosphate salts are employed as dehalocarbonylating agent, it is most preferable to conduct the process at temperatures of from about 200° C. to about 300° C.

Contact times between dehalocarbonylating agent and intermediate mixture in the preferred embodiment of step (b) are established principally by the dehalocarbonylation agent and temperature employed, and the desired conversion of the intermediate mixture to the product mixture. Generally, the intermediate mixture is contacted with the dehalocarbonylating agent from 0.01 to 10 minutes, and preferably from 1 to 60 seconds. Contact times may be controlled quite effectively when using a bed type reactor by means of suitable gas flow-metering devices for the input of gaseous intermediate mixture and a carrier or dilution gas such as nitrogen or carbon dioxide. Variation of the particle size of the dehalocarbonylating agent in the bed offers a further means of regulating the contact time. The dehalocarbonylating agent is consumed in the reaction and is preferably finely divided to ensure intimate contact with the intermediate mixture. In the instance where sodium carbonate ($Na_2CO_3$) and/or trisodium phosphate ($Na_3PO_4$) are employed as dehalocarbonylating agent, useful particle sizes range from 50 microns to 1 cm and are preferably from 10microns to 5 mm.

Since the dehalocarbonylating agent is consumed in the process of step (b) with the stoichiometry of the dehalocarbonylation reaction requiring one mole of dehalocarbonylating reagent per mole of PMPF and PEPF in the intermediate mixture, the quantity of available dehalocarbonylating agent is preferably at least stoichiometric with the intermediate mixture. Most preferably, an excess of dehalocarbonylating agent is used to ensure maximum conversion of the intermediate mixture to product mixture. Although the agent may be present in quantities less than stoichiometric with the intermediate mixture, this method of operation is not normally utilized since larger quantities of unconverted intermediate mixture must be handled.

The reactor in which the gas-solid phase dehalocarbonylation is carried out is preferably constructed from a material which is inert to the reactants and conditions employed. Moreover, the apparatus should be equipped with suitable means for temperature control to maintain the reaction temperature within the prescribed limits so as to minimize by-product formation. Especially suitable both for facilitating contacting of dehalocarbonylating agent with intermediate mixture and control of process temperature is the use of standard fluidized bed or stirred bed techniques such as those discussed in Chemical Reaction and Reaction Engineering by L. Doraswamy and B. Kulkarni, published by Marcel Dekker, Inc., NY, 1987, edited by J. Carberry and A. Varma. Fluidization of the finely divided dehalocarbonylating agent may be achieved by means of the vaporized intermediate mixture alone or in combination with an inert carrier gas such as nitrogen or carbon dioxide. Stirring and agitation of the bed may be carried out through use of known methods.

A second embodiment for the contacting the PMPF and PEPF of the intermediate mixture and the dehalocarbonylating agent in step (b) of the present invention involves use of a polar aprotic solvent. A significant feature of this method is that the reaction temperature may be substantially decreased from that employed in the previous method in which gaseous intermediate mixture is contacted with a solid phase dehalocarbonylating agent. For example, when carrying out the reaction in a solvent phase, product mixture can be obtained from intermediate mixture and dehalocarbonylating agent at reaction temperatures as low as 75° C. It is preferred that the dehalocarbonylation process carried out in solvent employ a temperature range of from 100° C. to 200° C. Useful solvents are polar aprotic solvents such as ethylene glycol dialkyl ethers of formula $C_rH_{2r+1}(OCH_2CH_2)_sOC_rH_{2r+1}$ wherein r=1–3 and s=1–6, dimethyl sulfoxide, N-methylpyrolidone, hydrocarbon nitriles, N,N-dimethyl formamide and other N,N-dialkyl amides and alkylaryl ketones. Particularly preferred as solvents in this embodiment of step (b) are ethylene glycol dimethyl ether ($CH_3OCH_2CH_2OCH_3$) and ethylene glycol diethyl ether ($CH_3CH_2OCH_2CH_2OCH_2CH_3$). The polar aprotic solvents may be further described as those which are capable of dissolving at least 0.01 weight % of an alkali metal salt of a perfluoro 2-alkoxypropionic acid at 25° C.

An alternate method for dehalocarbonylation of the intermediate mixture in step (b) to produce the product mixture comprising PMVE and PEVE is disclosed by Farnham in U.S. Pat. No. 5,268,511, issued Dec. 7, 1993, and Farnham in U.S. Pat. No. 5,391,796, issued Feb. 21, 1995. The chemistry disclosed by Farnham involves a two step process for producing fluoroalkyl perfluorovinyl ethers from fluorinated carboxylic acid fluorides in which the acid fluorides are reacted with a siloxane in the first step, followed by heating in the presence of a thermolysis catalyst in the second step to produce a fluoroalkyl perfluorovinyl ether.

In the preferred process of the invention employing $Na_2CO_3$ and/or $Na_3PO_4$ as the decarbonylation agent, PMVE and PEVE is produced in high yield. Consequently, if the intermediate mixture used does not contain high percentages of impurities, the product mixture obtained upon dehalocarbonylation typically also contains few side products and impurities. However, it is generally desirable, however, to remove $CO_2$ from the mixture and also water if water is present in substantial quantity.

The mixture of PMVE and PEVE as obtained in the process can be used directly as a comomomer mixture for use in the manufacture of fluoropolymers. If desired, PMVE and PEVE can be easily separated by distillation to recover the vinyl ethers separately.

One preferred configuration of apparatus for the practice of the present invention is shown schematically in FIG. 1. The apparatus depicted is useful for an initial mixture of CF and PAF obtained by oxidation of a perfluoroolefin such as a by-product stream obtained from the liquid phase reaction of $O_2$ with HFP to make HFPO.

With reference to FIG. 1, the initial mixture containing CF and PAF is first fed to distillation column 1. Volatile components such as $O_2$ are removed at vent 2 in distillation column 1, optionally with a portion of CF. This may be used to provide a constant mole ratio of CF/PAF and also serves to reduce the pressure. The initial mixture is transferred from distillation column 2 through line 3 to reactor 4. Reactor 4 is initially charged with acetonitrile solvent and tetraethyl ammonium bromide catalyst. As required, fresh solvent and catalyst mixed with solvent are added to reactor 4 through line 6. Reactor 4 is surrounded by jacket 7 containing an appropriate heat-transfer medium for maintaining constant reaction temperature. HFPO is added to reactor 4 via line 5. Reactor 4 is further fitted with mechanical agitator 8 for mixing of reactor contents.

Liquid reaction phase is transferred from reactor 4 via line 9 to decanter 10. A less dense phase containing solvent, dissolved catalyst, initial mixture and intermediate mixture separates and is returned to reactor 4 via line 11. Reactor 4 is fitted with headspace port 12 for venting small quantities of reactor gaseous phase which allows closer control over the reactor total pressure. The instantaneous contents and conditions within reactor 4 are maintained as has been described previously. The more dense fluorocarbons comprising CF, PAF, HFPO, PMPF, PEPF and HFPO oligomers are further cooled in decanter 10 to a temperature near −25° C. to further separate dissolved solvent. Such solvent is returned to reactor 4 via line 11 and the fluorocarbons are fed via line 13 to stripper column 14. The high boiling components from stripper column 14 are transferred via line 15 to acid fluoride column 16, and the low boiling components comprising unreacted CF, PAF and HFPO are returned via line 17 to reactor 4. Acid fluoride column 16 separates the desired intermediate mixture comprising PMPF and PEPF from other reaction products such as HFPO oligomers which are discharged at line 18 for treatment as waste. Low boilers comprising intermediate mixture are taken from acid fluoride column 16 via line 19 to decanter 20 which further serves to separate the intermediate mixture from solvent which is discharged for treatment as waste through line 21. Intermediate mixture comprising PMPF and PEPF is transferred via line 22 for storage in acid fluoride tank 23 until required in step (b) of the process.

Intermediate mixture is fed from acid fluoride storage tank 23 via line 24 to bed reactor 25. Bed reactor 25 contains dehalocarbonylating agent $Na_2CO_3$ and gaseous intermediate mixture is allowed to contact the agent at 230° C. Fresh dehalocarbonylating agent is fed at line 26 to bed reactor 25 and spent dehalocarbonylating reagent is removed at line 27 which allows for continuous operation of the bed. The product mixture comprising PMVE and PEVE, and in addition, 2 moles of $CO_2$ per mole of the product mixture, is removed from bed reactor via line 28 and fed into scrubber 29. Scrubber 29 contains an aqueous solution of caustic which serves to remove $CO_2$ from the product mixture. Fresh caustic solution is added via line 30 and spent caustic solution is removed via line 31. The product mixture is transferred via line 32 from scrubber 29 to dryer 33. Dryer 33 contains a common solid absorbent with high affinity for water such as molecular sieves which serve to remove water from the product mixture. The product mixture is transferred via line 34 from dryer 33 to compressor 35 which serves to compress the product mixture from gaseous to liquid state for transfer via line 36 and storage in product mixture storage tank 37.

The PMVE/PEVE product mixture may be discharged from storage tank 37 at line 42 for use as a mixture or transferred via line 38 to distillation column 39 for separation into individual components with PMVE being discharged at line 40 and PEVE being discharged at line 41.

EXAMPLES

The following examples are offered to further illustrate the present invention.

Fluorine nuclear magnetic resonance spectroscopy (fluorine NMR) referred to in the following examples is a standard analysis technique for fluorinated compounds. This technique is described by T.S. Everett in Chemistry of Organic Fluorine Compounds II—A Critical Review, edited by M. Hudlicky and A. Pavlath, published by the American Chemical Society, Washington, D.C., 1995, chapter 7, section three titled Nuclear Magnetic Resonance Spectroscopy of Organofluorine Compounds, pages 1037–1086.

Example1 —Production of an Intermediate Mixture Comprising PMPF and PEPF from HFPO and an Initial Mixture Comprising CF and PAF A dry 360 cc HASTELLOY® C shaker tube is charged with 0.4 g ($2\times10^{-3}$ mol) $N(CH_2CH3)Br$ and 80 ml anhydrous acetonitrile. The shaker tube is sealed, cooled to $-78°$ C. and taken through two evacuation/nitrogen purge cycles. While cooling at $-78°$ C., 21 g (0.32 mol) CF, 25 g (0.22 mol) PAF, and 70 g (0.42 mol) HFPO are charged to the shaker tube by vacuum transfer. The tube is then warmed to $35°$ C. and maintained for 8 hours with vigorous shaking. After this period, the tube is cooled to $-20°$ C. and the contents added to excess chilled methanol.

Carbolylic acid fluorides and HFPO are well known in the art to react quantitatively with methanol to produce methyl esters. In the instance of the present example, methyl esters of the carboxylic acid fluorides and unreacted HFPO in the reaction mixture are easier to manipulate and analyze due to their higher boiling points. Analysis of the carboxylic acid fluoride/methanol reaction mixture by fluorine NMR revealed four major products:

(a)—$CF_3OCF(CF_3)CO_2CH_3$ PMPF/methanol adduct (b)—$CF_3CF_2OCF(CF_3)CO_2CH_3$ PEPF/methanol adduct (c)—$CF_3CF_2CF_2OCF(CF_3)CO_2CH_3$ HFPO dimer/methanol adduct (d)—$CF_3CF(OCH_3)CO_2CH_3$ HFPO/methanol adduct Esters of corresponding PMPF/HFPO and PEPF/HFPO adducts arising from reaction of PMPF and PEPF with HFPO are not observed. Comparison of peak areas from integrated fluorine NMR signals revealed a relative mole ratio of product esters of 6.7(a):2.3(b):1.0(c), which is equivalent to 2.9(PMPF):1(PEPF). As the initial charge of CF/PAF is 1.5:1 (66.7 mole % excess CF versus PAF), the relative ratio of the rate at which CF reacted with HFPO versus the rate at which PAF reacted with HFPO is 1.9 (CF) :1 (PAF).

Example 2—Production of a Product Mixture Comprising PMVE and PEVE by Contacting a Mixture Comprising PMPF and PEPF with a Stirred Bed of $Na_2CO_3$ at $225°$ C.

A cylindrical, carbon steel, stirred reactor is packed with $Na_2CO_3$ of 0.1 mm average particle size. Stirring is begun and the $Na_2CO_3$ charge is then heated at $290°$ C. for 5 hours under a flow of dry nitrogen to remove trace amounts of water from the system. The temperature of the bed is then brought to $225°$ C. and the dry nitrogen flow replaced with dry $CO_2$ flow. PMPF and PEPF are then fed to the reactor as a 99% pure, 7:3 mole ratio mixture of PMPF:PEPF. The average contact time of the perfluoroorganics with the $Na_2CO_3$ bed is 1 minute. The mole ratio of the $Na_2CO_3$ charge to the PMPF+PEPF charge is 1.3:1. The gaseous effluent exiting the reactor is scrubbed through aqueous caustic, dried over molecular sieves and condensed. The product mixture so obtained is a 99% pure, 2.3:1 mole ratio mixture of PMVE:PEVE. The molar yields of PMVE (based on PMPF) and PEVE (based on PEPF) in this mixture are 90% and 89% respectively. The product mixture also contained traces (less than 1 mole %) of $CF_3CF_2CF_2OCF=CF_2$.

What is claimed is:

1. A process for producing perfluoromethyl perfluorovinyl ether (PMVE) and perfluoroethyl perfluorovinyl ether (PEVE) comprising the steps of:

(a) contacting an initial mixture comprising carbonyl fluoride (CF) and perfluoroacetyl fluoride (PAF) with hexafluoropropylene epoxide (HFPO) under conditions which form a mixture comprising 2,3,3,3-tetrafluoro-2-(trifluoromethoxy)propionic acid fluoride (PMPF) and 2,3,3,3-tetrafluoro-2-(pentafluoroethoxy)propionic acid fluoride (PEPF); and (b) dehalocarbonylating an intermediate mixture comprising 2,3,3,3-tetrafluoro-2-(trifluoromethoxy)propionic acid fluoride (PMPF) and 2,3,3,3-tetrafluoro-2-(pentafluoroethoxy)propionic acid fluoride (PEPF) formed in step (a) to form a product mixture comprising perfluoromethyl perfluorovinyl ether (PMVE) and perfluoroethyl perfluorovinyl ether (PEVE).

2. The process of claim 1 wherein said initial mixture is formed by the reaction of a perfluorinated alkene with oxygen.

3. The process of claim 1 wherein said initial mixture is formed by the reaction of hexafluoropropylene (HFP) with oxygen.

4. The process of claim 1 wherein the temperature during said contacting of said initial mixture with hexafluoropropylene epoxide (HFPO) is about $20°$ C. to about $40°$ C.

5. The process of claim 1 wherein said contacting of said initial mixture with hexafluoropropylene epoxide (HFPO) is carried out in the presence of a polar aprotic solvent.

6. The process of claim 5 wherein said polar aprotic solvent is selected from the group consisting of acetonitrile, benzonitrile and mixtures thereof.

7. The process of claim 1 wherein said contacting of said initial mixture with hexafluoropropylene epoxide (HFPO) is carried out in the presence of a catalyst.

8. The process of claim 7 wherein said catalyst is a tetraalkyl ammonium halide represented by the formula

wherein $R^5$, $R^6$, $R^7$, $R^8$ are the same or different and are linear or branched $C_1$ through $C_4$ alkyl groups and X is fluoride, chloride, bromide, or iodide.

9. The process of claim 7 wherein said catalyst is $N(CH_2CH_3)_4Br$.

10. The process of claim 1 wherein the mole ratio in step (a) of the sum of the moles of carbonyl fluoride (CF) and perfluoroacetyl fluoride (PAF) with respect to the moles of hexafluoropropylene epoxide (HFPO) is at least about 1.

11. The process of claim 1 wherein the mole ratio in step (a) of the sum of the moles of carbonyl fluoride (CF) and perfluoroacetyl fluoride (PAF) with respect to the moles of hexafluoropropylene epoxide (HFPO) is at least about 1.5.

12. The process of claim 1 wherein the mole ratio in step (a) of the sum of the moles of carbonyl fluoride (CF) and perfluoroacetyl fluoride (PAF) with respect to the moles of hexafluoropropylene epoxide (HFPO) is about 2 to about 10.

13. The process of claim 1 wherein the mole ratio in step (a) of moles of carbonyl fluoride (CF) to perfluoroacetyl fluoride (PAF) is about 0.1 to about 10.

14. The process of claim 1 wherein the mole ratio in step (a) of moles of carbonyl fluoride (CF) to perfluoroacetyl fluoride (PAF) is about 0.3 to about 3.

15. The process of claim 1 further comprising separating said intermediate mixture from other components of said mixture formed in step (a) prior to said dehalocarbonylation in step (b).

16. The process of claim 1 wherein said dehalocarbonylation in step (b) is carried out by contacting said intermediate mixture with a dehalocarbonylating agent selected from the group consisting of alkali metal carbonates, alkali metal phosphates and mixtures thereof.

17. The process of claim 16 wherein said dehalocarbonylating agent is selected from the group consisting of $Na_2CO_3$ and $Na_3PO_4$ and mixtures thereof.

18. The process of claim 17 wherein the reaction temperature in step (b) is between 200° C. and 300° C.

* * * * *